US007922686B2

(12) United States Patent
Childers et al.

(10) Patent No.: US 7,922,686 B2
(45) Date of Patent: *Apr. 12, 2011

(54) SYSTEMS AND METHODS FOR PERFORMING PERITONEAL DIALYSIS

(75) Inventors: Robert W. Childers, Trinity, FL (US); Lee Pan, Tampa, FL (US); Brian Lauman, Clearwater, FL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 1390 days.

This patent is subject to a terminal disclaimer.

(21) Appl. No.: 10/624,150

(22) Filed: Jul. 17, 2003

(65) Prior Publication Data
US 2004/0019320 A1 Jan. 29, 2004

Related U.S. Application Data

(60) Provisional application No. 60/397,268, filed on Jul. 19, 2002.

(51) Int. Cl.
*A61M 1/00* (2006.01)
(52) U.S. Cl. ............................................ 604/29; 604/28
(58) Field of Classification Search .................. 604/4.01, 604/5.01, 6.11, 27, 28, 29, 30, 93.01
See application file for complete search history.

(56) References Cited

U.S. PATENT DOCUMENTS

| | | | |
|---|---|---|---|
| 2,529,028 A | 7/1947 | Landon | |
| 2,122,509 A | 7/1948 | Beliaeff | |
| 3,332,737 A | 7/1967 | Krause | |
| 3,388,803 A | 6/1968 | Scott | |
| 3,463,728 A | 8/1969 | Kolobow et al. | |
| 3,485,245 A | 12/1969 | Lahr et al. | |
| 3,490,479 A | 1/1970 | Mott et al. | |
| 3,545,438 A | 12/1970 | De Vries | |
| 3,608,729 A | 9/1971 | Haselden | |
| 3,617,545 A | 11/1971 | Dabois et al. | |
| 3,619,423 A | 11/1971 | Galletti et al. | |
| 3,667,612 A | 6/1972 | Leonard | |

(Continued)

FOREIGN PATENT DOCUMENTS

DE 19828923 A1 1/2000

(Continued)

OTHER PUBLICATIONS

Roberts et al. "Innovative peritoneal dialysis: flow-thru and dialysate regeneration". ASAIO Journal. Sep. 1999. vol. 45(5): 372-378.*

(Continued)

*Primary Examiner* — Kevin C Sirmons
*Assistant Examiner* — Laura C Schell
(74) *Attorney, Agent, or Firm* — K&L Gates LLP

(57) ABSTRACT

Systems and methods for providing multiple pass continuous flow dialysis therapy are provided. The present invention includes a fluid circuit connected to a patient via a catheter thereby defining a fluid loop along which a therapy fluid including a dialysate can be continuously circulated into, through and out of a peritoneal cavity of a patient to remove a therapeutically effective amount of excess water and solutes including uremic toxins. The feed rate and discharge rate of therapy fluid into the fluid loop can be controllably regulated in proportion to the circulation rate of fluid in the fluid loop such that the therapy fluid can pass a multiple number of times along the fluid loop prior to discharge.

19 Claims, 7 Drawing Sheets

U.S. PATENT DOCUMENTS

| | | |
|---|---|---|
| 3,669,878 A | 6/1972 | Marantz et al. |
| 3,669,880 A | 6/1972 | Marantz et al. |
| 3,682,817 A | 8/1972 | Marx |
| 3,697,418 A | 10/1972 | Johnson |
| 3,703,959 A | 11/1972 | Raymond |
| 3,707,967 A | 1/1973 | Kitrilakis et al. |
| 3,727,612 A | 4/1973 | Sayers et al. |
| 3,730,183 A | 5/1973 | Goldsmith et al. |
| 3,799,873 A | 3/1974 | Brown |
| 3,809,241 A | 5/1974 | Alvine |
| 3,825,493 A | 7/1974 | Brown et al. |
| 3,850,835 A | 11/1974 | Marantz et al. |
| 3,878,564 A | 4/1975 | Yao et al. |
| 3,884,808 A | 5/1975 | Scott |
| 3,911,915 A | 10/1975 | Seifter et al. |
| 3,926,797 A | 12/1975 | Gigou et al. |
| 3,939,069 A | 2/1976 | Granger et al. |
| 3,979,284 A | 9/1976 | Granger et al. |
| 3,989,622 A | 11/1976 | Marantz et al. |
| 4,000,072 A | 12/1976 | Sato et al. |
| 4,031,010 A | 6/1977 | Nose |
| 4,036,747 A | 7/1977 | Hori et al. |
| 4,081,372 A | 3/1978 | Atkin et al. |
| 4,115,259 A | 9/1978 | Bigi |
| 4,118,314 A | 10/1978 | Yoshida |
| 4,173,537 A | 11/1979 | Newhart et al. |
| 4,180,460 A | 12/1979 | Calari |
| 4,190,047 A | 2/1980 | Jacobsen et al. |
| 4,191,646 A | 3/1980 | Larsson et al. |
| 4,192,748 A | 3/1980 | Hyden |
| 4,194,536 A | 3/1980 | Stine et al. |
| 4,212,738 A | 7/1980 | Henne |
| 4,213,859 A | 7/1980 | Smakman et al. |
| 4,240,408 A | 12/1980 | Schael |
| 4,247,393 A | 1/1981 | Wallace |
| 4,256,718 A | 3/1981 | McArthur et al. |
| 4,267,047 A | 5/1981 | Henne et al. |
| 4,269,708 A | 5/1981 | Bounomini et al. |
| 4,276,175 A | 6/1981 | Bower |
| 4,293,762 A | 10/1981 | Ogawa |
| 4,303,521 A | 12/1981 | Lehmann |
| 4,313,831 A | 2/1982 | Lehmann et al. |
| 4,338,190 A | 7/1982 | Kraus et al. |
| 4,360,507 A | 11/1982 | McArthur et al. |
| 4,364,747 A | 12/1982 | Blackshear et al. |
| 4,381,003 A | 4/1983 | Buoncristiani |
| 4,460,555 A | 7/1984 | Thompson |
| 4,464,563 A | 8/1984 | Jewett |
| 4,473,449 A | 9/1984 | Michaels et al. |
| 4,498,900 A | 2/1985 | Buoncristiani |
| 4,532,414 A | 7/1985 | Shah et al. |
| 4,542,015 A | 9/1985 | Smakman et al. |
| 4,581,141 A | 4/1986 | Ash |
| 4,586,920 A | 5/1986 | Peabody |
| 4,618,343 A | 10/1986 | Polashegg |
| RE32,303 E | 12/1986 | Lasker et al. |
| 4,650,857 A | 3/1987 | May |
| 4,661,246 A | 4/1987 | Ash |
| 4,678,460 A | 7/1987 | Rosner |
| 4,680,445 A | 7/1987 | Ogawa |
| 4,684,460 A | 8/1987 | Issautier |
| 4,703,913 A | 11/1987 | Hunkapiller |
| 4,718,890 A | 1/1988 | Peabody |
| 4,735,609 A | 4/1988 | Comeau et al. |
| 4,747,822 A | 5/1988 | Peabody |
| 4,765,907 A | 8/1988 | Scott |
| 4,769,151 A | 9/1988 | Shouldice |
| 4,804,474 A | 2/1989 | Blum |
| 4,844,074 A | 7/1989 | Kurucz |
| 4,847,470 A | 7/1989 | Bakke |
| 4,906,816 A | 3/1990 | van Leerdam |
| 4,976,683 A | 12/1990 | Gauthier et al. |
| 5,004,459 A | 4/1991 | Peabody et al. |
| 5,073,167 A | 12/1991 | Carr et al. |
| 5,125,069 A | 6/1992 | O'Boyle |
| 5,141,492 A | 8/1992 | Dadson et al. |
| 5,141,493 A * | 8/1992 | Jacobsen et al. ............... 604/29 |
| 5,180,896 A | 1/1993 | Gibby et al. |
| 5,245,693 A | 9/1993 | Ford et al. |
| 5,277,820 A | 1/1994 | Ash |
| 5,284,470 A | 2/1994 | Beltz |
| 5,336,173 A | 8/1994 | Folden |
| 5,338,293 A | 8/1994 | Jeppsson et al. |
| 5,350,357 A | 9/1994 | Kamen et al. |
| 5,370,674 A | 12/1994 | Farrell |
| 5,381,510 A | 1/1995 | Ford et al. |
| 5,408,576 A | 4/1995 | Bishop |
| 5,420,962 A | 5/1995 | Bakke |
| 5,438,510 A | 8/1995 | Bryant et al. |
| 5,474,683 A | 12/1995 | Bryant et al. |
| 5,498,338 A | 3/1996 | Kruger et al. |
| 5,542,919 A | 8/1996 | Simon et al. |
| 5,641,405 A | 6/1997 | Keshaviah et al. |
| 5,643,201 A | 7/1997 | Peabody et al. |
| 5,645,734 A | 7/1997 | Kenley et al. |
| 5,683,381 A | 11/1997 | Carr et al. |
| 5,685,988 A | 11/1997 | Malchesky |
| 5,690,614 A | 11/1997 | Carr et al. |
| 5,722,947 A | 3/1998 | Jeppsson et al. |
| 5,724,478 A | 3/1998 | Thweatt |
| 5,729,653 A | 3/1998 | Magliochetti et al. |
| 5,744,042 A | 4/1998 | Strange et al. |
| 5,762,782 A | 6/1998 | Kenley et al. |
| 5,776,091 A * | 7/1998 | Brugger et al. ............... 604/6.1 |
| 5,790,752 A | 8/1998 | Anglin et al. |
| 5,816,779 A | 10/1998 | Lawless et al. |
| 5,836,908 A | 11/1998 | Beden et al. |
| 5,858,238 A | 1/1999 | McRea et al. |
| 5,873,853 A | 2/1999 | Keilman et al. |
| 5,875,282 A | 2/1999 | Jordan et al. |
| 5,902,336 A | 5/1999 | Mishkin |
| 5,919,369 A | 7/1999 | Ash |
| 5,921,951 A | 7/1999 | Morris |
| 5,938,634 A | 8/1999 | Packard |
| 5,944,684 A | 8/1999 | Roberts et al. |
| 5,960,160 A | 9/1999 | Clark et al. |
| 5,980,481 A | 11/1999 | Gorsuch |
| 5,984,891 A | 11/1999 | Keilman et al. |
| 5,989,238 A | 11/1999 | Ginsburg |
| 5,989,423 A | 11/1999 | Kamen et al. |
| 6,069,343 A | 5/2000 | Kolowich |
| 6,074,359 A | 6/2000 | Keshaviah et al. |
| 6,129,699 A | 10/2000 | Haight et al. |
| 6,139,528 A | 10/2000 | Kistner et al. |
| 6,142,974 A | 11/2000 | Kistner et al. |
| 6,146,359 A | 11/2000 | Carr et al. |
| 6,168,578 B1 | 1/2001 | Diamond |
| 6,175,688 B1 | 1/2001 | Cassidy et al. |
| 6,193,684 B1 | 2/2001 | Burbank et al. |
| 6,196,992 B1 | 3/2001 | Keilman et al. |
| 6,210,361 B1 | 4/2001 | Kamen et al. |
| 6,220,299 B1 | 4/2001 | Arvidsson et al. |
| 6,228,047 B1 | 5/2001 | Dadson |
| 6,229,957 B1 | 5/2001 | Baker |
| 6,234,991 B1 | 5/2001 | Gorsuch |
| 6,234,992 B1 | 5/2001 | Haight et al. |
| 6,236,809 B1 | 5/2001 | Cassidy et al. |
| 6,245,039 B1 | 6/2001 | Brugger et al. |
| 6,254,567 B1 * | 7/2001 | Treu et al. ............... 604/29 |
| 6,261,261 B1 | 7/2001 | Gordon |
| 6,261,809 B1 | 7/2001 | Bertling et al. |
| 6,290,669 B1 | 9/2001 | Zicherman |
| 6,293,921 B1 | 9/2001 | Shinmoto et al. |
| 6,302,653 B1 | 10/2001 | Bryant et al. |
| 6,409,699 B1 * | 6/2002 | Ash ............... 604/29 |
| 6,666,842 B1 * | 12/2003 | Sakai ............... 604/29 |
| 2001/0041873 A1 | 11/2001 | Dopper et al. |

FOREIGN PATENT DOCUMENTS

| | | |
|---|---|---|
| DE | 19814695 C2 | 9/2001 |
| EP | 64393 | 11/1982 |
| EP | 152717 | 8/1985 |
| EP | 0243547 B1 | 7/1991 |
| EP | 0402505 B1 | 12/1993 |
| EP | 0498382 B1 | 11/1996 |
| EP | 0778033 A2 | 11/1996 |
| EP | 0575512 BI | 5/1998 |

| | | |
|---|---|---|
| EP | 0928615 A1 | 7/1999 |
| EP | 0956876 A1 | 11/1999 |
| EP | 980685 | 2/2000 |
| EP | 0659092 B1 | 10/2000 |
| EP | 0847769 B1 | 8/2001 |
| GB | 2122509 | 1/1984 |
| GB | 2124511 | 2/1984 |
| JP | 55-32384 | 3/1980 |
| JP | 92002060 | 1/1992 |
| JP | 4348757 | 3/1992 |
| JP | 07-299455 | 11/1995 |
| JP | 8029224 | 2/1996 |
| JP | 96029224 | 2/1996 |
| JP | 9327511 | 12/1997 |
| JP | 10085324 | 4/1998 |
| JP | 11137672 | 5/1999 |
| JP | 200120483 | 12/2000 |
| SE | 1012918 | 3/1981 |
| SE | 1344362 | 6/1984 |
| WO | WO94/20158 | 9/1994 |
| WO | WO95/02559 | 1/1995 |
| WO | WO95/35124 | 12/1995 |
| WO | WO97/47337 | 6/1997 |
| WO | WO98/17333 | 4/1998 |
| WO | WO99/03519 | 1/1999 |
| WO | WO99/06082 | 2/1999 |
| WO | WO 99/06082 * | 2/1999 |
| WO | WO00/20050 | 4/2000 |
| WO | WO00/20052 | 4/2000 |
| WO | WO00/50143 | 8/2000 |
| WO | WO00/57928 | 10/2000 |

OTHER PUBLICATIONS

Vychytil et al. "The role of tidal peritoneal dialysis in modern practice: a european perspective". Kidney International. 2006. vol. 70: S96-S103.*

"Fresnius 90/2 Peritoneal Therapy Cylcer" Article, written by Fresenius USA, dated Jul. 1993.

Ronco article entitled "Continuous Flow Peritoneal Dialysis: Is There a Need for it?" *Seminars in Dialysis*, vol. 14, No. 5, (Sep.-Oct. 2001), pp. 395-400.

Roberts et al. article entitled "Innovative Peritoneal Dialysis: Flow-Thru and Dialysate Regeneration" *ASAIO Journal*, 1999, pp. 372-378.

* cited by examiner

SYSTEMS AND METHODS FOR PERFORMING PERITONEAL DIALYSIS

PRIORITY CLAIM

This application claims the benefit of U.S. Provisional Patent Application No. 60/397,268, filed Jul. 19, 2002, entitled "Systems And Methods For Performing Peritoneal Dialysis", the entire contents of which are hereby incorporated by reference and relied upon.

BACKGROUND OF THE INVENTION

The present invention generally relates to systems and methods for providing peritoneal dialysis. More specifically, the present invention relates to systems and methods for providing continuous flow peritoneal dialysis.

Due to disease, insult or other causes, a person's renal system can fail. In renal failure of any cause, there are several physiological derangements. The balance of water, minerals and the excretion of daily metabolic load is no longer possible in renal failure. During renal failure, toxic end products of nitrogen metabolism (e.g., urea, creatinine, uric acid, and others) can accumulate in blood and tissues.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving. One who has failed kidneys could not continue to live without replacing at least the filtration functions of the kidneys.

Hemodialysis and peritoneal dialysis are two types of dialysis therapies commonly used to treat loss of kidney function. Hemodialysis treatment removes waste, toxins and excess water directly from the patient's blood. The patient is connected to a hemodialysis machine and the patient's blood is pumped through the machine. For example, needles or catheters can be inserted into the patient's veins and arteries to connect the blood flow to and from the hemodialysis machine. As blood passes through a dialyzer in the hemodialysis machine, the dialyzer removes the waste, toxins and excess water from the patient's blood and returns the blood to infuse back into the patient. A large amount of dialysate, for example about 90-120 liters, is used by most hemodialysis machines to dialyze the blood during a single hemodialysis therapy. The spent dialysate is then discarded. Hemodialysis treatment lasts several hours and is generally performed in a treatment center about three times per week.

Another type of hemodialysis therapy is regenerative hemodialysis. This therapy uses a hemodialysis system, which includes a cartridge for dialysate regeneration. One such cartridge is manufactured under the name REDY™ by Sorb Technology, Oklahoma City, Okla. In this system, the dialysate fluid flow path must be properly cleaned before the hemodialysis machine can be used on another patient. Also, the dialysate fluid flow path is not a closed system. In this regard, the dialysate fluid flow path is open to the atmosphere such that air borne pathogens can contact the fluid in the system and foster the growth of bacteria in same. Consequently, contamination of such a dialysis system can be problematic. Thus, the dialysate fluid exiting the REDY™ cartridge is not suitable for peritoneal dialysis.

Peritoneal dialysis utilizes a sterile dialysis solution or "dialysate", which is infused into a patient's peritoneal cavity and into contact with the patient's peritoneal membrane. Waste, toxins and excess water pass from the patient's bloodstream through the peritoneal membrane and into the dialysate. The transfer of waste, toxins, and excess water from the bloodstream into the dialysate occurs due to diffusion and osmosis during a dwell period as an osmotic agent in the dialysate creates an osmotic gradient across the membrane. The spent dialysate is later drained from the patient's peritoneal cavity to remove the waste, toxins and excess water from the patient.

There are various types of peritoneal dialysis therapies, including continuous ambulatory peritoneal dialysis ("CAPD") and automated peritoneal dialysis. CAPD is a manual dialysis treatment, in which the patient connects the catheter to a bag of fresh dialysate and manually infuses fresh dialysate through the catheter and into the patient's peritoneal cavity. The patient disconnects the catheter from the fresh dialysate bag and allows the dialysate to dwell within the cavity to transfer waste, toxins and excess water from the patient's bloodstream to the dialysate solution. After a dwell period, the patient drains the spent dialysate and then repeats the manual dialysis procedure. Tubing sets with "Y" connectors for the solution and drain bags are available that can reduce the number of connections the patient must make. The tubing sets can include pre-attached bags including, for example, an empty bag and a bag filled with dialysate.

In CAPD the patient performs several drain, fill, and dwell cycles during the day, for example, about four times per day. Each treatment cycle, which includes a drain, fill and dwell, takes about four hours. Manual peritoneal dialysis performed by the patient requires a significant amount of time and effort from the patient. This procedure leaves room for improvement and therapy enhancements to improve patient quality of life.

Automated peritoneal dialysis is similar to continuous ambulatory peritoneal dialysis in that the dialysis treatment includes a drain, fill, and dwell cycle. However, a dialysis machine automatically performs three to four cycles of peritoneal dialysis treatment, typically overnight while the patient sleeps.

With automated peritoneal dialysis, an automated dialysis machine fluidly connects to an implanted catheter. The automated dialysis machine also fluidly connects to a source or bag of fresh dialysate and to a fluid drain. The dialysis machine pumps spent dialysate from the peritoneal cavity, through the catheter, to the drain. The dialysis machine then pumps fresh dialysate from the dialysate source, through the catheter, and into the patient's peritoneal cavity. The automated machine allows the dialysate to dwell within the cavity so that the transfer of waste, toxins and excess water from the patient's bloodstream to the dialysate solution can take place. A computer controls the automated dialysis machine so that the dialysis treatment occurs automatically when the patient is connected to the dialysis machine, for example, when the patient sleeps. That is, the dialysis system automatically and sequentially pumps fluid into the peritoneal cavity, allows for dwell, pumps fluid out of the peritoneal cavity, and repeats the procedure.

Several drain, fill, and dwell cycles will occur during the treatment. Also, a smaller volume "last fill" is typically used at the end of the automated dialysis treatment, which remains in the peritoneal cavity of the patient when the patient disconnects from the dialysis machine for the day. Automated peritoneal dialysis frees the patient from having to manually perform the drain, dwell, and fill steps during the day. Automated dialysis can improve the patient's dialysis treatment and undoubtedly improves the patient's quality of life as compared to CAPD.

"Continuous flow" peritoneal dialysis ("CFPD") systems have been contemplated since the 1970's. These systems typically have an in fluid flow and an out fluid flow. That is, the dialysate flows in one catheter lumen, through the peritoneum and out another catheter lumen to the drain line. The "spent" dialysate (waste laden dialysate) collects in a drain bag, which is discarded, or is fed into a household or other drain. Known CFPD systems typically use a volume of disalysate one time and then discard it. In this regard, the volume of dialysate necessary to carry out treatment for a continuous flow single use or single pass system can be large in size rendering their daily use cost prohibitive. For example, the volume of dialysate can exceed 120 liters for single pass CFPD systems.

Another type of a CFPD system is disclosed in U.S. Pat. No. 3,707,967. This system requires the use of a reconstitution device to remove waste from the dialysate after the dialysate has passed through the patient's peritoneum. In particular, the reconstitution device includes a urea removal column that employs urease to enzymatically convert urea into ammonia. The ammonia must then be removed from the dialysate prior to reintroduction into the peritoneal cavity in order to ensure the health and safety of the patient. However, the removal of ammonia can be problematic and thus may not provide a failsafe measure. Moreover, additional sensors must be employed to monitor the removal of ammonia from the reconstitued dialysate. This can add to the complexity of the therapy and thus increase the cost associated with same.

In general, CFPD is known to be more effective as compared to other forms of peritoneal dialysis therapy including, for example, more conventional forms of peritoneal dialysis therapies, such as CAPD and APD which typically require multiple exchanges of fresh dialysate during treatment. As previously discussed, several drain, fill and dwell cycles are typically performed during CAPD and APD. An example of a modification of the more conventional forms of peritoneal dialysis therapy is disclosed in U.S. Pat. No. 4,618,343. An apparatus is disclosed that allows the peritoneal cavity of the patient to be filled with a sterile dialysis liquid as in the case of CAPD. After a dwell period, the dialysis liquid retains metabolic waste from the patient's blood. A portion of the dialysis liquid containing the metabolic waste is then pumped out of the peritoneal cavity and passed through a dialyzer to remove the metabolic waste from the dialysis liquid. The dialysis liquid can then be pumped back into the peritoneal cavity for reuse.

Therefore, a need exists to provide improved dialysis systems. Particularly, a need exists to provide closed loop dialysis systems that can reuse spent dialysate. The systems should allow the patient to perform the procedure at home without the need for storing an inordinate amount of fresh dialysate bags. The systems should further be automated so that the procedure can be largely performed at night while the patient sleeps.

SUMMARY OF THE INVENTION

In general, the present invention relates to dialysis therapy. In particular, the present invention provides systems and methods that can perform continuous flow dialysis therapy, such as during peritoneal dialysis.

The continuous flow dialysis therapy systems and methods of the present invention include, in general, a fluid circuit connected to a patient thereby defining a fluid loop or path such that dialysate or other suitable therapy fluid can be circulated into, through and out of the patient's peritoneum to remove a therapeutic effective amount of excess water, solutes including uremic toxins and/or the like.

In an embodiment, the dialysate is fed at a feed rate and discharged at a discharge rate as it is circulated at a circulation rate, preferably continuously circulated, along the fluid loop. The feed rate, discharge rate and circulation rate can be controllably regulated such that the dialysate is capable of circulating a multiple number of times along the fluid loop, and thus reused, prior to discharge. In this regard, the volume of dialysate can be effectively minimized while maintaining, it is believed, solute clearances, such as urea, creatinine or the like, at or exceeding clinically acceptable standards.

The feed rate and discharge rate, in an embodiment, can be maintained at an approximately equal rate that is less than the circulation rate. In this regard, the number of times that the dialysate can circulate along the fluid loop can be increased in proportion to the ratio of the feed rate or the discharge rate to the circulation rate. For example, if the circulation rate is approximately two times greater than both of the feed rate and the discharge rate, the dialysate is capable of making about two passes along the fluid loop prior to discharge. In an embodiment, the dialysate is capable of making about two, three or any other suitable number of passes in the fluid loop prior to discharge.

The present invention can be automated in order to enhance, for example, the quality of life issues associated with patient use. In general, the flow of dialysate can be controllably regulated. For example, a cycler can be used to automatically control the flow of dialysate into and out of the fluid loop thus eliminating the need for the patient to manually exchange a number of supply bags of dialysate during treatment. In an embodiment, the cycler includes a multi-path fluid circuit coupled to a pumping mechanism and a series of valves to provide automatic control of the dialysate flow into and out of the fluid loop.

In an embodiment, the dialysate can be cleaned prior to recirculation into, through and out of the peritoneum of the patient. This can facilitate the removal of solutes and excess water from the patient. In this regard, the volume of dialysate necessary to provide effective treatment can be further minimized due to cleaning of the dialysate prior to reuse. In an embodiment, a sorbent material that is capable of non-selective removal of solutes from the dialysate can be used. This type of material can include, for example, carbon, activated charcoal and/or other suitable materials.

The present invention can also be adapted to accommodate for an increase in volume of therapy fluid during treatment. In this regard, the volume of therapy fluid including the amount of fresh dialysate fed into the circulation fluid loop is optimally utilized. For example, the present invention can be adapted to accommodate for an increase in therapy fluid volume due to the addition of ultrafiltrate which can pass into the fluid loop as the dialysate is circulated into, through and out of the peritoneum of the patient. In this regard, the addition of ultrafiltrate to the fluid circuit, in effect, can increase the capacity to remove solutes by keeping the additional volume in contact with the fluid loop.

An advantage of the present invention is to provide improved systems and methods for providing dialysis therapy.

Another advantage of the present invention is to provide improved systems and methods for continuous flow peritoneal dialysis.

Yet another advantage of the present invention is to provide systems and methods that can reuse therapy fluid including dialysate during treatment.

Yet still another advantage of the present invention is to provide systems and methods of dialysis therapy that can effectively minimize or reduce the amount of dialysate necessary for effective treatment.

A further advantage of the present invention is to provide improved systems and methods for performing dialysis therapy which can be safely and conveniently administered to a patient in a home setting.

Yet a further advantage of the present invention is to provide systems and methods that can circulate the dialysate a multiple number of times into, through and out of a peritoneum of the patient while the dialysate is fed and discharged at a controlled rate in proportion to the circulation rate of the dialysate.

Yet still a further advantage of the present invention is to provide systems and methods that can accommodate for an increase in therapy fluid volume such that the therapy fluid including dialysate can be optimally utilized during treatment.

Additional features and advantages of the present invention are described in, and will be apparent from, the following Detailed Description of the Invention and the Figures.

DETAILED DESCRIPTION OF THE INVENTION

Figure 1:
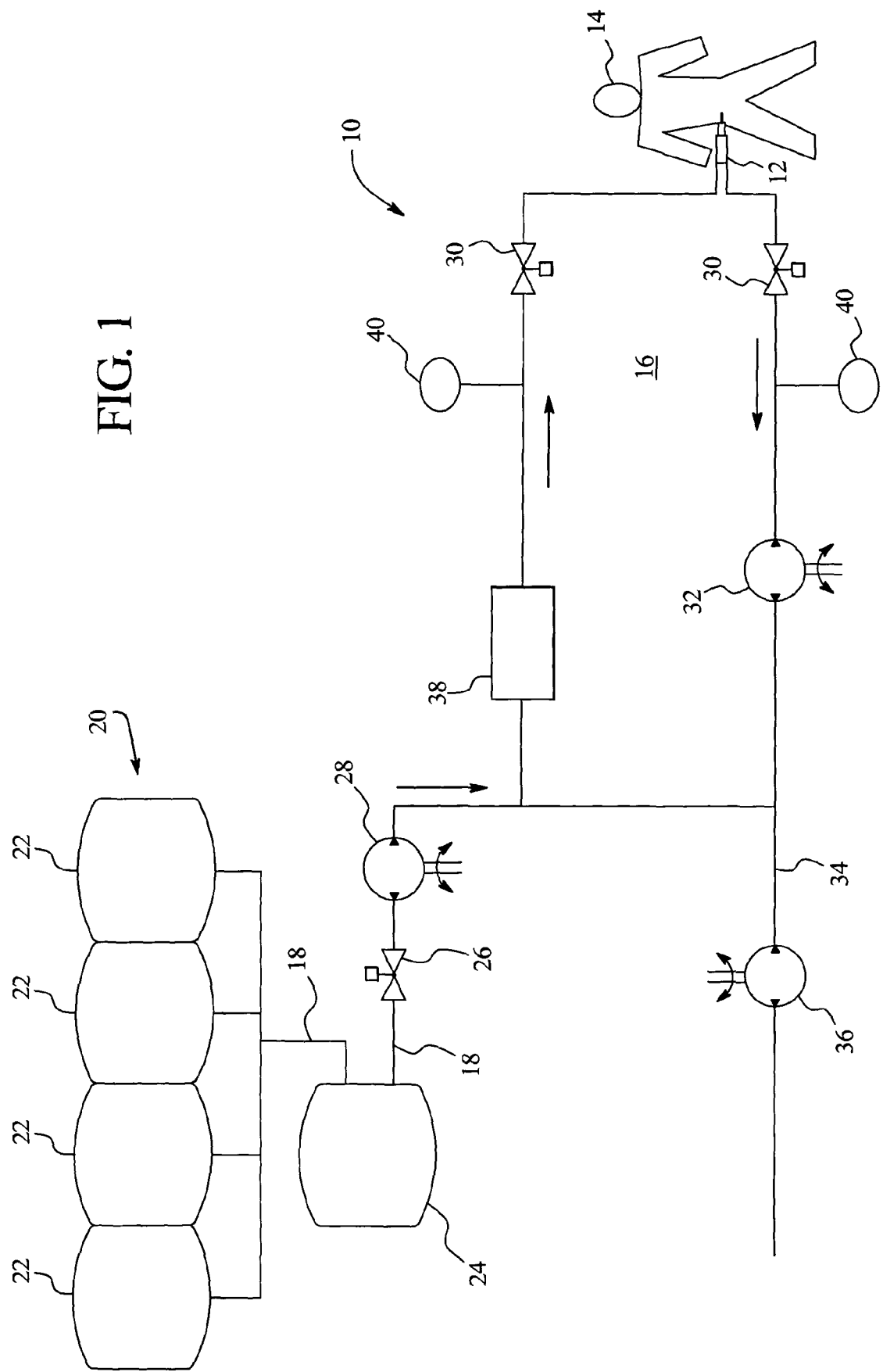
FIG. 1 schematically illustrates an embodiment of the present invention.

In general, the present invention includes a fluid circuit connected to a dialysis patient thereby defining a fluid loop such that dialysate can be fed into, circulated along and discharged from the fluid loop during treatment. As the dialysate is circulated along the fluid loop, it passes into, through and out of a peritoneal cavity or peritoneum of the patient connected to the fluid loop. This effectively removes excess water (e.g., ultrafiltrate), solutes including uremic toxins, such as urea, creatinine and uric acid and/or other like constituents from the patient's blood.

In an embodiment, the flow rate of the dialysate is controllably regulated as it is fed into, circulated along and discharged from the fluid loop such that the dialysate can make a multiple number of passes along the circulation or fluid loop prior to discharge. In this regard, the volume of dialysate can be minimized while maintaining effective clearance levels of solutes, such as creatinine and urea. As compared to conventional single throughput continuous flow dialysis therapies, it is believed that at least one half of the amount of dialysate is necessary for effective treatment. Thus, cost savings can be realized since a lesser amount of dialysate is necessarily required during treatment.

As used herein, the term "continuous flow" or other like terms as applied to dialysis therapy, such as peritoneal dialysis, means that the therapy fluid including dialysate is constantly and simultaneously flowing into and out of the patient's peritoneum during treatment. In this regard, the dwell period of the dialysate inside the peritoneum associated with typical peritoneal dialysis therapies, such as CAPD and APD, is effectively eliminated.

It should be appreciated that the continuous fluid flow of the present invention can include any suitable level of intermittent, non-continuous batch, tidal or the like fluid flow during treatment. For example, the present invention may provide for brief intermittent fluid flow, such as during the filling of a pump chamber, the fluid loop, the patient and/or the like prior to treatment, brief periods of downtime or breaks in therapy and/or other like suitable conditions. In this regard, the present invention can be controlled to provide a variety and number of suitable dialysis therapies, as desired. Accordingly, even though the dialysis system can provide continuous flow, the present invention can also include non-continuous flow or batch systems and processes. In an embodiment, the continuous flow into through and out of the peritoneal cavity preferably occurs during the main therapy treatment, so that a dwell during a last bag, for example, does not detract from the continuous flow feature.

The dialysis systems and methods of the present invention provide advantages compared to other dialysis systems and therapies, such as clinical advantages, economic advantages, and quality of life advantages, for example. It is believed that the present invention has clinical advantages, such as, improved blood pressure control, improved fluid volume control, improved therapy performance as assessed by known clinical standards, such as the National Kidney Foundation's DOQI standard, higher clearance efficiency rates, lower glucose absorption, glucose profiling and ultrafiltrate management, reduced catheter channeling and the like.

It is also believed that the present invention can provide economic advantages, such as, reduced therapy cost when compared to single pass CFPD. Further, it is believed that present invention has quality of life advantages, such as, increased awake time free from dialysis devices, improved patient access, reduced complexity, reduced self-administration of drugs, reduced therapy training, elimination of the need for having a home water infrastructure, a reduced amount of fluid that the patient must handle and manage, simpler prescriptions and elimination of patient transportation to dialysis centers.

The dialysis systems and methods of the present invention more closely simulate and replace continuous kidney functioning as compared to intermittent dialysis therapies. This, in turn, can contribute to improved clinical outcomes while minimally impacting the patient's lifestyle. The efficiency and convenience of the present invention provides patients with a renal replacement therapy that is relatively unrestrictive. This allows patients to have greater freedom from limitations experienced by dialysis devices and therapies. The present invention can provide easier entrance into early dialysis therapy because the system can enable the physician to monitor therapy while minimally impacting the patient's lifestyle.

The continuous flow dialysis systems and methods of the present invention can include a variety of different components and configurations to effectively remove solutes and excess water from the patient while minimizing the amount of dialysate necessary for effective treatment. As shown in FIG. 1, the present invention includes a fluid circuit 10 in fluid communication with a catheter 12 insertable within a patient 14 undergoing peritoneal dialysis. This defines a fluid loop 16 along which dialysate can be continuously circulated into, through and out of the patient's peritoneum to effectively remove excess water and solutes including uremic toxins, such as urea, creatinine and uric acid and/or other like constituents from the patient during treatment.

Catheter

Any suitable catheter or other medically acceptable access device can be utilized. In a preferred embodiment, a dual lumen catheter having an in flow lumen and an out flow lumen can be used. The dual lumen catheter provides for continuous flow into through and out of the peritoneal cavity of the patient. To this end, the dual lumen catheter is implanted in the patient. An example of a catheter for use in the dialysis system of the present invention is disclosed in U.S. patent application Ser. No. 09/689,508, filed on Oct. 12, 2000, and entitled "Peritoneal Dialysis Catheter," the disclosure of which is incorporated herein by reference. However, it should be noted that two single lumen catheters can be used as well as a single lumen catheter.

In general, the dialysate is fed into, circulated within and discharged, preferably in a continuous manner, from the fluid loop during treatment at respective feed, circulation and discharge rates. It should be appreciated that the supply of dialysate into the fluid loop and the discharge of dialysate out of the fluid loop may occur intermittently in addition to continuously during treatment. For example, after the initial fill of the fresh source of dialysate into the fluid loop including the patient, the dialysate may be allowed to circulate along the fluid loop without infusion of an additional amount of dialysate into the fluid loop and without discharge of fluid from the fluid loop. This initial circulation period can occur for any suitable amount of time, such as for about 30 minutes at the beginning of therapy. After the initial circulation period, the dialysate can then be fed into and drained from the fluid loop for the remaining treatment time, preferably in a continuous manner.

In an embodiment, the feed, circulation and discharge rates are controllably regulated such that the dialysate can circulate a multiple number of times into and out of the patient's peritoneum prior to discharge during treatment. This can minimize the amount of dialysate that is necessary for effective treatment, particularly as compared to conventional continuous flow dialysis therapies that utilize a single throughput or single pass of dialysate into, through and out of the peritoneum.

In an embodiment, the feed rate and the discharge rate are maintained at an approximately equal rate that is less than the circulation rate. This causes the dialysate to pass through the fluid loop a multiple number of times that is approximately equal to the circulation rate divided by the feed rate or discharge rate. For example, if the feed rate and the discharge rate are about one half of the circulation rate, the dialysate can pass about two times along the fluid loop prior to discharge. In an embodiment, the dialysate can circulate about two times, three times or any suitable number of times in approximate proportion to the circulation rate divided by the feed rate or discharge rate.

The feed rate, circulation rate and the discharge rate can be controllably maintained or regulated in any suitable manner. In an embodiment, the dialysate is fed into the fluid loop via a supply fluid path 18 connected to the fluid loop. As shown in FIG. 1, a fresh source of dialysate 20 is contained in four separate supply containers 22 which are each coupled to a chamber 24 along the supply fluid path. The chamber 24 can be adapted to heat the fresh source of dialysate before it passes into the circulation fluid loop 16. As discussed below, in-line heating is provided in certain embodiments. It should be appreciated, however, that the present invention is also operable with a batch type of heating, wherein, for example, one or more of the supply containers 22 is heated prior to therapy. A valve 26 and supply pump 28 are positioned downstream of the chamber 24 to regulate the flow of fresh dialysate into the fluid loop 16. It should be appreciated that any suitable valve, pump and/or other suitable device can be utilized to regulate flow.

Dialysate

The fresh source of dialysate solution can include any suitable type of dialysate solution, preferably those types of solutions that are particularly suited for peritoneal dialysis therapy. In an embodiment, the fresh source of dialysate solution includes an osmotic agent, such as dextrose or the like in any suitable effective amount. It should be appreciated that the amount of dextrose necessary for effective therapy may vary from patient to patient. In this regard, the amount of osmotic agent can vary and include any clinically acceptable level, such as about 1.5%, about 2.5%, about 3.5%, about 4.25% or greater to meet the specific needs of the patient. The dialysate can include any suitable amount and type of electrolytes in addition to the osmotic agent including, for example, calcium, sodium, potassium, like constituents and combinations thereof.

As previously discussed, the present invention can minimize the volume of dialysate necessary for effective treatment. In an embodiment, the amount of fresh dialysate necessary for treatment is about 25 liters or less. In a preferred embodiment, the fresh source of dialysate is stored in four separate container 22 each having a capacity of about 6 liters or less as shown in FIG. 1. It should be appreciated that the dialysate supply containers can include any suitable type of container, such as a bag composed of any suitable and medically acceptable material, such as any suitable type of plastic material.

Heater

As previously discussed, the chamber 24 can be adapted to heat the fresh source of dialysate before it is fed into the circulation fluid loop 16. In this regard, the temperature of the dialysate at initial system fill can be quite low, such as 5° C. to 10° C. if the fluid is stored in cold ambient temperature. In an embodiment, the fluid heater is an in-line heater (continuous flow heater) that heats the fluid to the desired temperature as the fluid flows continuously past the heater. In other embodiments, heaters other than in-line heaters can be used, for example, bulk heaters, a dual heater that can include both an infrared heater and a plate heater and other suitable heating devices.

In an embodiment, the fluid heater is a dual heater (not shown), including an infrared heater and a plate heater. An example of such a dual heater is disclosed in a patent application entitled, "Medical Fluid Heater Using Radiant Energy," Ser. No. 10/051,609, incorporated herein by reference. Both the infrared heater and the plate heater are in-line heaters that heat the medical fluid that flows continuously past the heaters. The radiant energy or infrared heater emits infrared energy that is directed to and absorbed by the fluid in the patient loop, thereby heating the fluid. The radiant energy or infrared heater is a primary or high capacity heater which can heat a relatively large volume of cold fluid to a desired temperature in a short period of time.

The plate heater is a secondary or maintenance heater which has a relatively low heating capacity relative to the infrared heater. The plate heater uses electrical resistance to increase the temperature of a plate that in turn heats the fluid flowing near the plate.

The heater which includes both high and low capacity heaters, provides an efficient heater design that accommodates various fluid heating requirements. For example, the radiant or infrared heater is particularly useful for quickly heating cool dialysate (high heat energy demand) that is supplied to the dialysis system, such as at the initial system fill or if there is severe heat loss during dialysis treatment. The temperature of the dialysate at initial system fill can be quite low, such as 5° C. to 10° C. if the fluid is stored in cold ambient temperature.

The plate heater is particularly useful to maintain a desired temperature (lower heat energy demand) of the fluid being supplied to the patient, e.g., due to a normal amount of heat loss during dialysis treatment. The infrared heater provides for the high heat demand in a small amount of fluid exposure space, while the plate heater provides for maintenance heat demand and requires a lesser amount of input energy compared to the infrared or radiant heater. Furthermore, the heating capacity of the heater is increased if both the infrared and plate heaters and are used together to heat the fluid.

The infrared heater and the plate heater can be arranged in various configurations relative to each other. The heaters in an embodiment are arranged so that the fluid passes by the heaters sequentially (e.g., first the radiant or infrared heater and then the plate heater or vice versa). In an embodiment, the fluid passes by the heaters simultaneously (both heaters at the same time). The fluid flow path past the heaters can be a common flow path for both heaters or include independent flow paths for each heater. Besides radiant or infrared electrical resistance heating, other types of heating such as convective, microwave, infrared ("IR") or inductive heating may be used.

In an embodiment, temperature sensors (not shown) can be provided at desired locations, such as along the fluid loop. The temperature sensors can monitor various fluid temperatures which can be utilized to control the fluid temperatures associated with the heater. When two or more heaters, such as an infrared heater and a plate heater, are provided, the system in an embodiment includes separate temperature sensors for each heater so that each heater can be controlled individually.

Once fed into the fluid loop, the dialysate is circulated at a certain circulation rate. The circulation rate of the dialysate into, through and out of the patient's peritoneum can be controlled in any suitable manner. As shown in FIG. 1, a number of valves 30 in addition to a single pump 32 are positioned along the fluid loop 16 to control the flow of therapy fluid including dialysate. In an embodiment, the circulation rate is maintained at about 300 ml/min or less, preferably ranging from about 100 ml/min to about 200 ml/min.

After the dialysate has passed along the fluid loop a multiple number of times, the dialysate is then drained from the fluid loop via a discharge fluid path 34 connected to the fluid loop 16 as shown in FIG. 1. A pump 36 is connected to the discharge path to control the discharge rate of the dialysate.

Monitors

It should be appreciated that the systems and methods of the present invention can utilize any suitable number and type of components to facilitate effective treatment of the patient in order to enhance quality of life, economic, treatment efficiency and other like treatment conditions and parameters. For example, the present invention can utilize any number and suitable types of devices to monitor the fluid loop during treatment. In an embodiment, the present invention can include any suitable number and type of devices which are capable of monitoring for the presence of air, moisture and other environmental contaminants in the fluid loop. In an embodiment, the present invention can include a gas sensor 38 to monitor for atmospheric gases including oxygen and carbon dioxide. If detected, the present invention can include any suitable device to remove the gas from the system of the present invention such that the gas can be vented to the atmosphere. This may be necessary to prevent contamination, such as bacterial contamination to the therapy fluid.

The present invention in embodiment can also include various other sensors to monitor various other suitable parameters. For example, pressure sensors 40 can be coupled to fluid loop to monitor the pressure at certain points along the fluid loop as shown in FIG. 1. This information can then be communicated to a controller (not shown) such that adjustments can be made to the pumps, valves and the like in order to obtain and maintain desired fluid pressures in the loop running into and out of the patient.

In an embodiment, the pressure sensors are non-invasive pressure sensors. These pressure sensors do not physically contact (and possibly contaminate) the medical fluid or dialysate. Of course, other fluid flow measurement devices, such as flow rate sensors, pressure gauges, flowmeters, pressure regulators, orifice plates, mass flow meters capacitive fluid sensors or other suitable flow measuring devices known to those of skill in the art may be provided in any suitable quantity and adapted to the fluid circuit.

In an embodiment, a flow measurement or volume sensing device is provided, which includes a capacitance sensor that measures the volume of fluid pumped through a chamber, such as a pump chamber (not shown). The capacitive fluid sensor is disclosed in greater detail in the patent application entitled, "Capacitance Fluid Volume Measurement," Ser. No. 10/054,487, incorporated herein by reference.

The capacitance C between two capacitor plates changes according to the function $C=k \times (S/d)$, wherein k is the dielectric constant, S is the surface area of the individual plates and d is the distance between the plates. The capacitance between the plates changes proportionally according to the function $1/(R \times V)$, wherein R is a known resistance and V is the voltage measured across the capacitor plates.

In an embodiment of the capacitance sensor, the sensor operates in cooperation with a cycler pump chamber. The cycler pump chamber in an embodiment includes shells or walls defining a fixed and known volume and a pair of flexible membranes operating between the shells, which expand to fill with fluid and contract to discharge fluid. The capacitance sensor includes capacitor plates disposed on opposite sides of the pump chamber. As the volume of fluid in the chamber or fluid pump changes (i.e., the pump chamber fills or empties), the dielectric property of the varying fluids between the capacitance plates changes. For example, the combined dielectric constant of dialysate and air changes as dialysate replaces air (or air replaces dialysate) within the constant volume shells of the chamber. This change in the overall dielectric constant affects a change in the capacitance plates, wherein a corresponding change in voltage can be sensed by a voltage sensing device. The controller monitors the changes in voltage by the voltage sensing device and correlates (after a calibration of the sensor) the capacitance change to an amount of fluid pumped through the chamber.

In another embodiment, the volume of the chamber or the pump chamber can vary, e.g., by movement of one or both the shells of the chamber. In this embodiment, the capacitance between the capacitor plates changes due to a changing distance d between the plates and/or a changing surface area S of one or more of the plates, wherein the dielectric constant k is static because only one fluid resides at all times between the capacitor plates. In a further alternative embodiment of the measurement device, the capacitance C between the capacitor plates changes based on any combination or all three of a change in dielectric constant k, distance d and surface area S.

The controller collects a multitude of voltage signals from capacitance changes due to a plurality of chamber fill and drain cycles, wherein the controller calculates a total volume of medical fluid pumped over a length of time or number of pump cycles. The capacitance sensor monitors the medical fluid, e.g., dialysate, flow into or from the pump chamber on a real time basis, and in a non-invasive manner.

The capacitance sensor enables the dialysis system to maintain the volume of fluid that is provided to the patient at desirable amounts and flow rates. Maintaining the fluid flow to the patient within desired levels is particularly advantageous for peritoneal dialysis therapies.

It is also desirable to maintain the fluid provided to the patient at proper physiologic levels. Physiologic control, such as sensing and/or adjusting parameters of the fluids, can take place at various locations in the dialysis system. To this end, the system can include any combination of a number of different types of physiologic level sensors. For example, the system can include one or more pH sensors. In one implementation, the cartridges explained below in connection with FIGS. 3A and 3B can include a pH sensor that helps to adjust the fluid so that it is maintained at a desired physiologic level.

Figure 2:
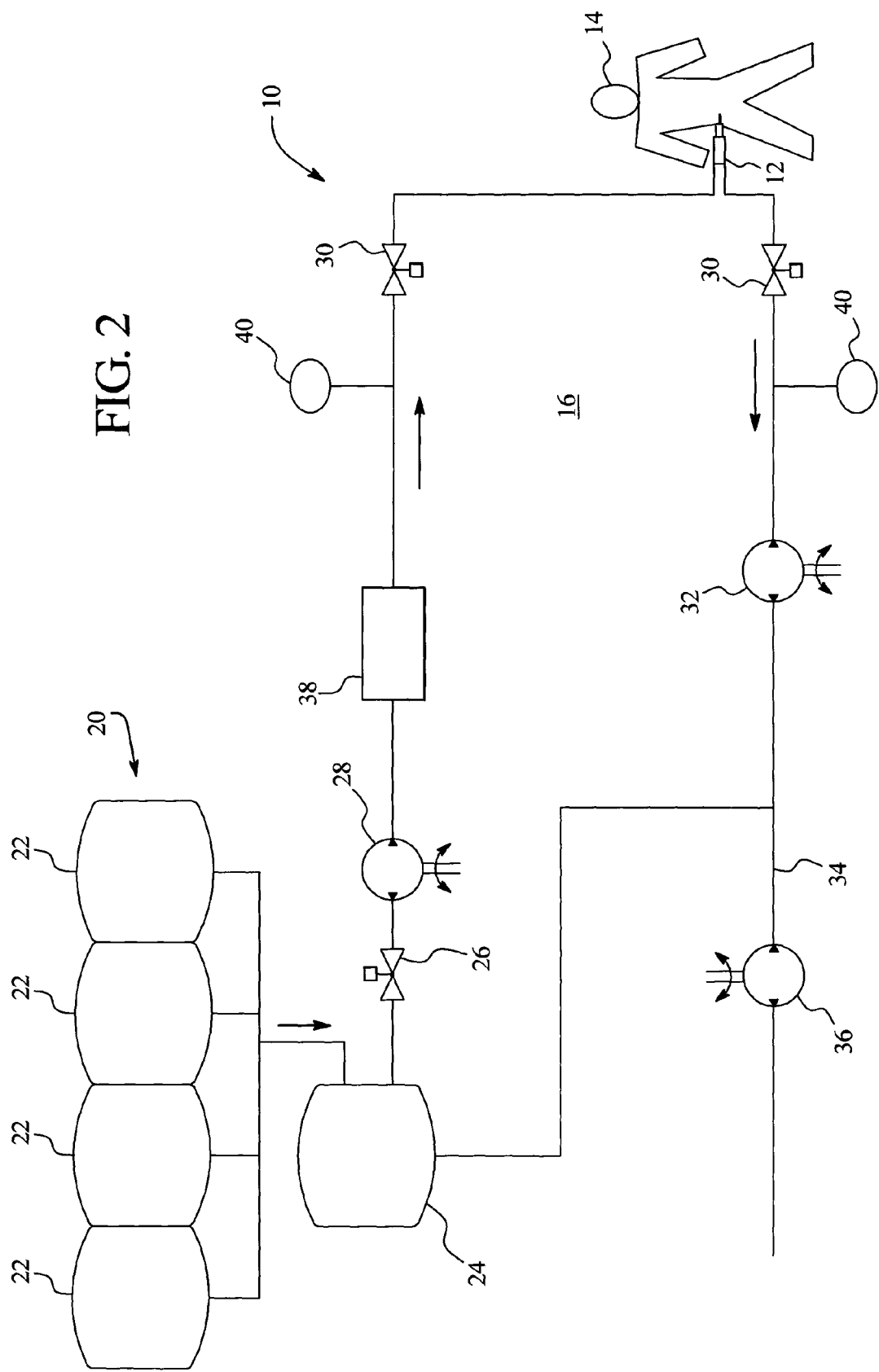
FIG. 2 schematically illustrates another embodiment of the present invention.

As illustrated in FIG. 2, the chamber 24 can be coupled directly to the fluid loop 16 such that the dialysate is capable of passing through the chamber 24 prior to recirculation into, through and out of the patient's peritoneum. In this regard, the chamber can be adapted both to heat the dialysate, particularly the fresh source of dialysate, and mix the fresh dialysate with the spent dialysate as it is circulated along the fluid loop. As used herein the term "fresh dialysate" or other like terms means any suitable amount and type of dialysate that is initially fed into the fluid loop prior to retaining any level of solutes and/or excess water from the patient. As used herein the term "spent dialysate" or other like terms means any suitable amount and type of dialysate that has circulated into, through and out of the peritoneum of the patient during treatment, and thus has retained a certain level of solutes and excess water from the patient.

Any suitable and various number of pumps, valves, sensing devices and other suitable fluid circuit components can be utilized to control the flow of dialysate such that it can pass a multiple number of times into and out of the patient's peritoneum prior to discharge. In an embodiment, the fluid circuit components used to control the dialysate flow are similar to the components shown in FIG. 1. As applied to FIG. 2, the number of times that the dialysate is capable of recirculation through the fluid loop is approximately equal to the feed rate divided by the difference between the circulation rate and the discharge rate. For example, if the feed rate is about 50 ml/min, the circulation rate is about 102 ml/min and the discharge rate is about 52 ml/min, the dialysate is capable of recirculation along the fluid loop approximately two times prior to discharge.

Variable Volume System

The present invention can utilize a number of different and suitable components to minimize the amount of dialysate necessary for effective treatment. For example, the present invention can be adapted to accommodate for a change in therapy fluid volume during treatment such that the use of the therapy fluid including the dialysate can be optimized. As used herein, the term "therapy fluid" or other like terms means any suitable fluid or solution that can be administered during dialysis therapy. The therapy fluids can include, for example, a fresh source of dialysate solution that has not been used during therapy, a waste or spent dialysate that contains solutes and metabolic waste removed from the patient during therapy, a clean source of dialysate that has been cleaned by sorbent materials or the like, a source of ultrafiltrate that has been passed from the patient to be mixed with the dialysate during treatment, a solution that includes an osmotic agent in a sufficient amount to enhance the diffusive properties of the therapy fluid, other suitable solutions and combinations thereof.

Figure 3A:
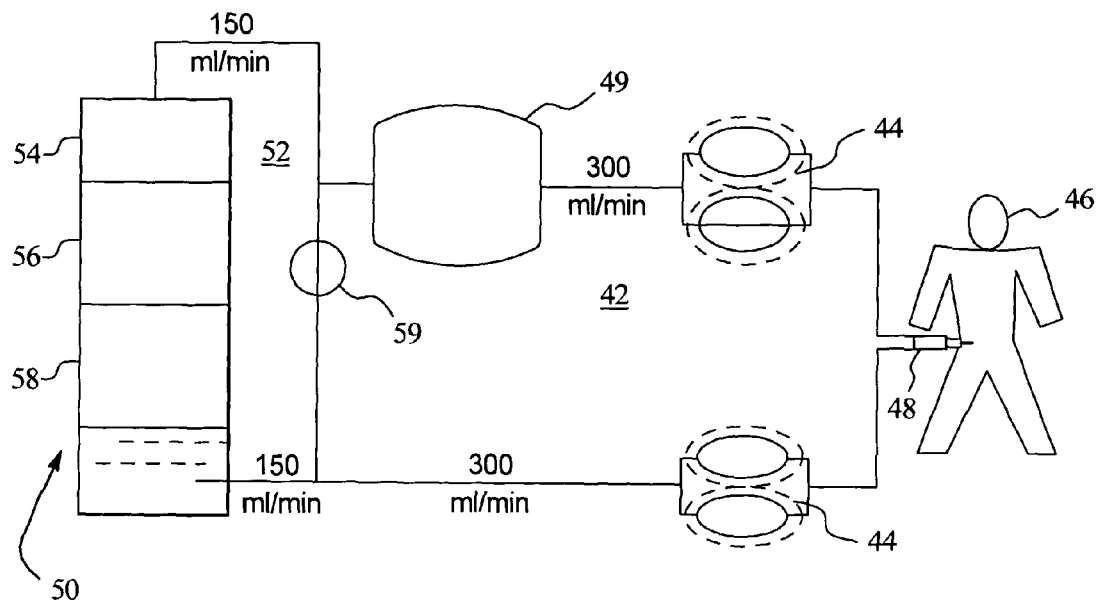
FIG. 3A schematically illustrate an embodiment of the present invention relating to variable volume systems employing four pumps.
Figure 3B:
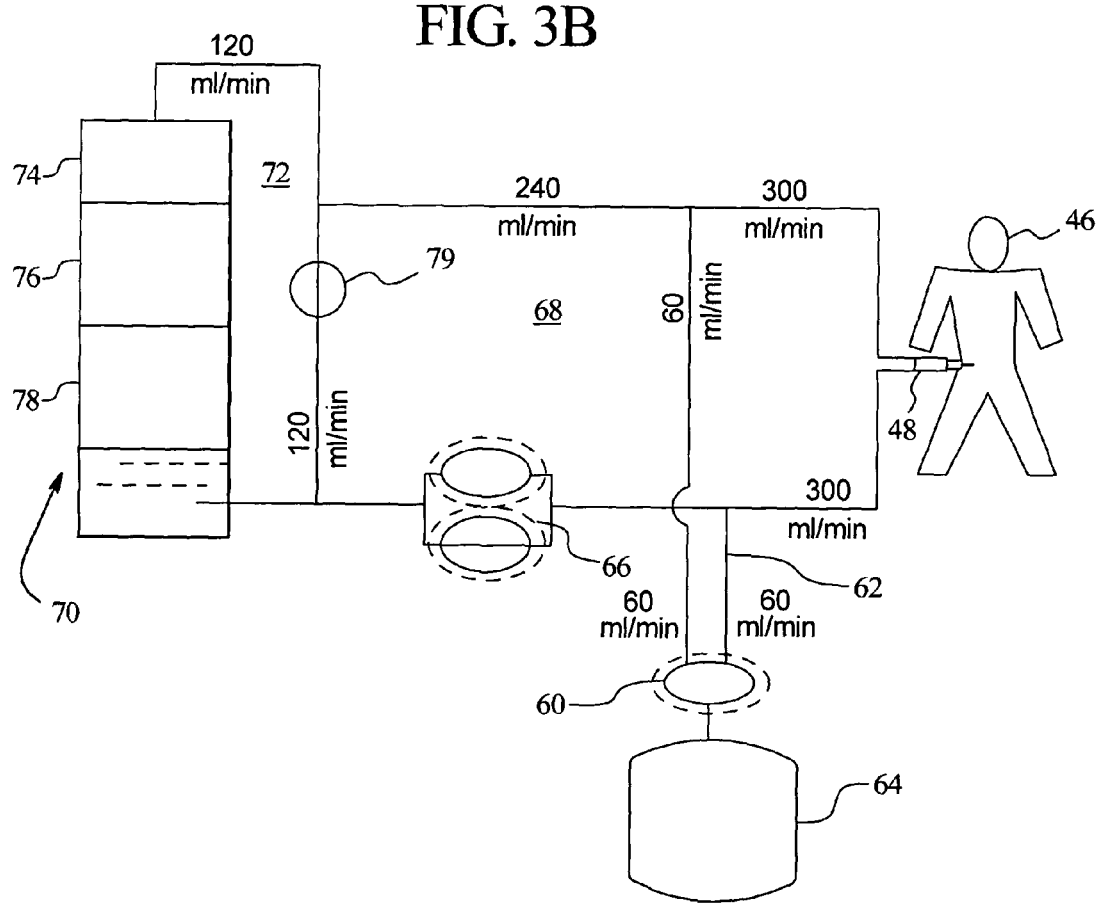
FIG. 3B schematically illustrate an embodiment of the present invention relating to variable volume systems employing three pumps.

In an embodiment, the present invention can be adapted to provide variable volume and continuous flow to the fluid loop connected to the patient as illustrated in FIGS. 3A and 3B. In this regard, the present invention can be adapted to accommodate for a variable increase in therapy fluid volume during treatment as previously discussed. The variable volume systems can include any suitable number of pumps, valves, fluid lines and/or the like to increase the available volume of therapy fluid during treatment. This is necessary to accommodate for an increase in available therapy fluid volume due to, for example, an amount of ultrafiltrate that passes to the fluid loop as the dialysate dialyzes the patient. The addition of ultrafiltrate and/or other suitable solutions to the fluid loop, in effect, can increase the capacity to remove solutes by keeping the additional volume in contact with the fluid loop. This can also have the effect of reducing the amount of fresh dialysate that is necessary for effective treatment.

Additional Osmotic Agent

In an embodiment, a fluid source which can be added in addition to the dialysate and ultrafiltrate can include one or more solutions, such as an aqueous solution that contains an osmotic agent, such as dextrose or the like, in a sufficient amount in order to replenish the diffusive properties of the therapy fluid during treatment. The amount of osmotic agent can include any suitable amount, such as about 2.5% by weight, about 3.5% by weight, about 4.25% or greater by weight and combinations thereof. The additional solution source can also include an acceptable level and type of constituents, such as electrolytes including calcium, magnesium, sodium, the like and combinations thereof, in addition to the osmotic agent. In an embodiment, an amount of a dextrose-based solution added to the fluid circuit is about 6 liters or less. The osmotic agent solution can be continuously fed or intermittently fed into the closed fluid path on a monitored basis in any suitable manner.

It should be appreciated that the amount and type of osmotic agent solution, such as a dextrose-based solution, necessary to facilitate effective treatment can vary from patient to patient. In an embodiment, a solution with a relatively high level of osmotic agent and electrolytes as compared to the existing therapy fluid can be fed to the fluid circuit in any suitable volumetric amounts, such as about 1 liter or less. In an embodiment, the solution concentrate of osmotic agent and electrolytes can include an osmotic agent, such as dextrose, at about 4.25% or greater by weight and concentration levels of electrolytes that are higher than existing levels in the therapy solution such that levels in the therapy solution can be adjusted to achieve optimal and physiological acceptable levels prior to reuse.

In an embodiment, components of the solution concentrate can be individually infused into the fluid loop. The components include those types of constituents typically contained in dialysate solutions including, for example, an osmotic agent, such as dextrose, bicarbonate, sodium, calcium, magnesium, like constituents and combinations thereof. The amount of individual components fed into the fluid loop can be regulated and controlled in any suitable manner.

As shown in FIG. 3A, the fluid loop 42 of the present invention can include two sets of two pumps in series 44. The sets of pumps 44 are positioned on the inflow side and the outflow side of the fluid path connected to the patient 46 via the catheter 48. The fluid loop 42 also includes a chamber 25 which can act to accumulate an increase in therapy fluid volume during treatment. The chamber can include any suitable device for accumulating therapy fluid, such as a bag typically used in dialysis therapy. As well, the fresh supply of dialysate (not shown) can be fed into the accumulator bag 49 during use. In this regard, the accumulator bag 49 can also be adapted to heat and/or mix the fresh dialysate with dialysate that circulates along the fluid loop. Alternatively, a separate chamber (not shown) can be coupled to the fluid loop through which a fresh source of dialysate can pass into the fluid loop as previously discussed.

In an embodiment, each pump can be run at about 150 ml/min to provide a circulation rate along the fluid loop of about 300 ml/min on average over time. In this regard, the pump rates can be desirably adjusted during treatment to allow for the accumulator bag 49 to have a sufficient amount of fluid capacity to accommodate for an increased volume of therapy fluid due to, for example, an influx of ultrafiltrate into the fluid loop as the dialysate passes into, through and out of the patient's peritoneum. It should be appreciated that the difference in the circulation rate into and out of the patient must not be too great so as to compromise the health and safety of the patient.

Cartridge

As previously discussed, the dialysate can be cleaned prior to recirculation into through and out of the patient's peritoneum. This can also be used to effectively minimize or reduce the amount of dialysate that is necessary for effective treatment. Any suitable type of device which utilizes any suitable amount and type of material to effectively clean the dialysate prior to reuse can be utilized. In an embodiment, the cleaning device includes a material that is capable of non-selective removal of solutes from the dialysate that have been removed from the patient during therapy. Preferably, the material includes any suitable sorbent material, such as carbon, activated carbon or other like material that is contained within a suitable housing, such as a cartridge, in any acceptable manner.

In an embodiment, the present invention can include other materials in addition to those types of materials which can non-selectively remove solutes from the dialysate. The additional other materials include, for example, materials that can selectively remove certain solutes or the like from solution. In an embodiment, the additional materials can include a binder or reactive sorbent material capable of selectively removing urea, a binder or reactive sorbent material capable of selectively removing phosphate and/or the like. As previously discussed, the use of materials capable of selective removal of solutes, particularly urea, can be used to enhance the cleaning efficiency of the system of the present invention such that the amount of dialysate necessary for effective treatment can be minimized.

The materials that can selectively remove solutes from solution, such as binder materials, can include a variety of suitable and different materials including, for example, polymeric materials that are capable of removing nitrogen-containing compounds, such as urea, creatinine, other like metabolic waste and/or the like in solution. In general, these types of materials contain a functional group(s) that chemically binds with urea or other like solutes.

For example, U.S. Pat. Nos. 3,933,753 and 4,012,317, each incorporated herein by reference, disclose alkenylaromatic polymers containing phenylglyoxal that can function to chemically bind urea. In general, the phenylglyoxal polymeric material is made via acetylation performed in, for example, nitrobenzene followed by halogenation of the acetyl group and treatment with dimethylsulfoxide as disclosed in U.S. Pat. Nos. 3,933,753 and 4,012,317. Another example of a polymeric material that is capable of selectively removing solutes, such as urea, from solution includes polymeric materials that contain a tricarbonyl functionality commonly known as ninhydrin as disclosed in U.S. Pat. No. 4,897,200, incorporated herein by reference. However, it should be appreciated that the present invention can include any suitable type of material or combinations thereof to selectively remove solutes, such as urea, from solution as previously discussed.

The cleaning cartridge of the present invention can include a number of components in addition to the sorbent materials capable of removing solutes from the dialysate. For example, the cleaning cartridge may have the capability to remove all or a portion of electrolytes, such as sodium, potassium, or the like, from the dialysate solution. In this case, an additional source of electrolytes in solution may be needed to replenish the dialysate after it has been cleaned. The cartridge may also be configured to release bicarbonate or the like into the system depending on the type of sorbent material used. This can facilitate pH regulation of the dialysate. As necessary, the cartridge may be filtered to prevent proteins, particulate matter or like constituents from leaching or exiting from the cartridge and into the dialysate.

As illustrated in FIG. 3A, a cleaning cartridge 50 can be coupled to the circulation loop 42 via a cleaning fluid loop 52. The cartridge 50 can include three separate layers, such as a layer of carbon 54, a layer of a phosphate binder 56 and a layer of a urea binder 58. The cleaning fluid path 52 can include a variable back pressure regulator 59 and/or other suitable components to control the flow through the cleaning fluid loop 52. In an embodiment, the rate of flow of the dialysate through the cleaning fluid loop, e.g., the cleaning flow rate, is less than the circulation rate. For example, the cleaning flow rate and the circulation rate can be maintained at 150 ml/mn and 300 ml/min, respectively.

FIG. 3B illustrates another embodiment of the variable volume system of the present invention. The system includes three pumps run at about 120 ml/min on average during the treatment period. The first pump 60 is coupled to a parallel fluid path 62 such that it can feed therapy fluid into and out of a chamber 64. A set of two pumps in series 66 is also coupled to the fluid loop 68. The pumps can be adjusted to control the circulation rate at any suitable rate, such as at a rate of about 300 ml/min flowing into, through and out of the patient's peritoneum as illustrated in FIG. 3B. A cleaning cartridge 70 can be coupled to the circulation fluid loop 68 via a cleaning fluid loop 72. The cleaning cartridge can include a layer of carbon 74, a phosphate binder 76 and a urea binder 78 as previously discussed. A back pressure regulator 79 can also be provided as previously discussed.

It should be appreciated that the uncertainty of volume of dialysate in the patient as it circulates along the fluid path can vary depending on the number and types of components used to control the circulation flow rate during treatment. For example, the uncertainty of dialysate volume in the patient during circulation is greater with respect to the four pump variable volume system as shown in FIG. 3A in comparison to the three pump variable volume system as shown in FIG. 3B. The patient volume uncertainty is an important consideration in the design of the continuous flow variable volume system. In this regard, the uncertainty provides an assessment of how much the patient volume can vary at any point in time during therapy. Adjustments in the system can then be made based on the uncertainty calculation such that the health and safety of the patient is not compromised.

As previously discussed, the present invention can be automated in order to eliminate the need for the patient to manually exchange bags of fresh dialysate during treatment. The automated feature is particularly beneficial for use in the evening or any other time of the day that the patient normally sleeps. The present invention can be automated in any suitable manner, such as by utilizing any number and suitable type of devices that can be adapted to automatically control the flow of therapy fluid including dialysate as it is continuously fed into, circulated within and discharged from the fluid loop.

Cycler

In an embodiment, the dialysate can be automatically fed into, circulated within and discharged from the fluid circuit with the use of a device which is commonly known in the art as a cycler. As used herein, the term "cycler" or other like terms refers to a pressure driven, diaphragm-type volumetric displacement pump or pumps coupled to a fluid path or paths in any suitable manner such that fluid flow can be automatically controlled. The cycler can determine the volume of liquid delivered as the difference in the volume of a pumping chamber before and after a pumping stroke. The pumping chamber, in general, includes two parts separated by a flexible diaphragm with air on one side and fluid on the other. Increasing the air pressure pushes liquid out of the chamber expanding the volume on the air side.

Examples of a cycler are disclosed in U.S. patent applications: "Peritoneal Dialysis Systems and Methods Employing a Liquid Distribution and Pumping Cassette That Emulates Gravity Flow," filed Mar. 3, 1993, Ser. No. 08/027,328, issued as U.S. Pat. No. 5,350,357; "Liquid Pumping Mechanisms for Peritoneal Dialysis Systems Employing Fluid Pressure," filed Mar. 3, 1993, Ser. No. 08/027,485, issued U.S. Pat. No. 5,431,626; "Peritoneal Dialysis Systems and Methods Employing Pneumatic Pressure and Temperature-Corrected Liquid Volume Measurements," filed on Mar. 3, 1993, Ser. No. 08/026,458, issued as U.S. Pat. No. 5,474,683; "Improved User Interface and Monitoring Functions for Automated Peritoneal Dialysis," filed Mar. 3, 1993, Ser. No. 08/025,531, issued as U.S. Pat. No. 5,438,510; "Improved User Interface for Automated Peritoneal Dialysis Systems," filed Mar. 3, 1993, Ser. No. 08/025,547, issued as U.S. Pat. No. 5,324,422; and "Peritoneal Dialysis Cycler," filed Mar. 3, 1993, Ser. No. 08/006,426, issued as U.S. Pat. No. D 351,470, the disclosures of all of which are incorporated herein by reference.

Figure 4A:
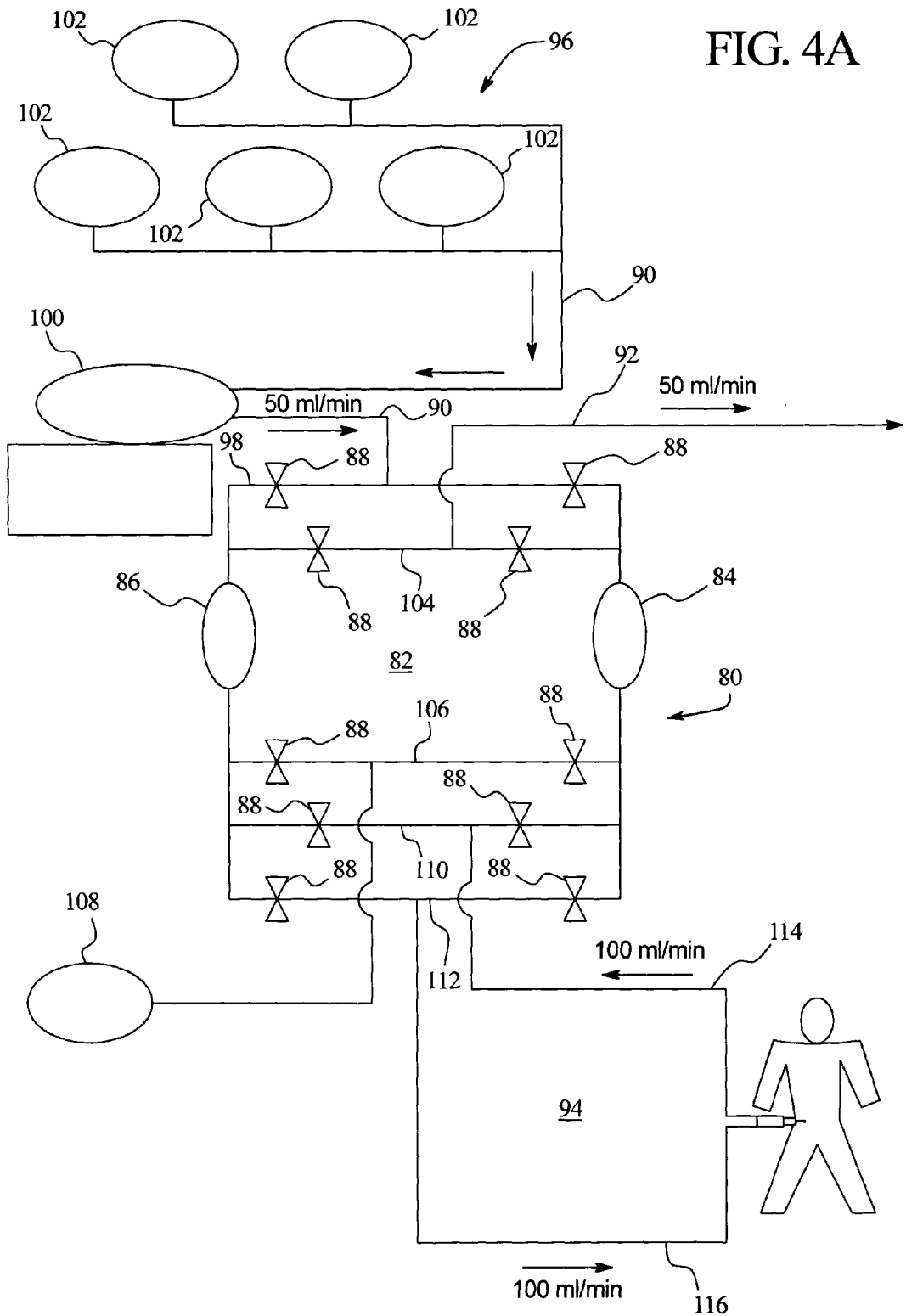
FIG. 4A schematically illustrates an embodiment of the present invention relating to a continuous flow system that utilizes a cycler adapted for automation without a cleaning fluid loop.

The fluid schematic 80 of the cycler in an embodiment of the present invention is illustrated in FIG. 4A. The cycler includes a multi-line fluid circuit 82 that has a first cycler pump 84, a second cycler pump 86 and a series of valves 88 coupled to the fluid lines in order to automatically control the flow of therapy fluid including dialysate. The automation of the cycler is provided by a controller (not shown) or any suitable other intelligence device. As shown in FIG. 4A, the dialysate supply path 90, discharge path 92 and circulation loop 94 is coupled to the multi-line fluid circuit 82 of the cycler that includes five separate fluid lines. The source of fresh dialysate 96 is coupled to the first fluid line 98 of the cycler via a chamber 100. The chamber 100 can act as a heater, mixer and/or accumulator as previously discussed.

In an embodiment, the fresh source of dialysate is stored in five separate containers 102 each in fluid communication with the chamber 100. The fresh dialysate containers each have a volume capacity of about 5 liters or less. In a preferred embodiment, about 25 liters or less of fresh dialysate is used during treatment. The second fluid line 104 of the cycler is coupled to the discharge fluid path 92. Once discharged, the dialysate can be disposed of or alternatively can be regenerated for prior use.

The third fluid line 106 of the cycler is coupled to a container 108 from which a fresh source of dialysate can be fed into the peritoneum cavity of the patient once the continuous flow therapy is complete. In this regard, the container 108 can act as a last bag of dialysate which can be administered to and dwell within the patient for an effective amount of time prior to discharge.

The fourth fluid line 110 and fifth fluid line 112 of the cycler are connected to the out flow 114 and in flow 116 fluid paths of the fluid loop 94 which is capable of circulating dialysate into through and out of the patient's peritoneum during continuous flow therapy. The cycler can be adapted to cause the dialysate to flow into the fluid loop, circulate within the loop and discharge after use, preferably in a continuous manner. In this regard, the dialysate flow is controlled to cause the dialysate to circulate within the fluid loop a multiple number of times before discharge. It should be appreciated that the cycler can be coupled to the continuous flow system in any suitable manner, such as with the use of any suitable disposable cartridge that can be used as a fluid interface between the patient and the fluid circuit to readily and easily couple the patient to the fluid circuit as typically employed during automated peritoneal dialysis and modifications thereof.

In an embodiment, the feed rate and discharge rate of the dialysate into and out of the fluid loop 94 is maintained at an approximately equal rate that is less than the circulation rate of the dialysate in the fluid loop. In this regard, the multiple number of times that the dialysate is capable of circulation within the fluid loop 94 is approximately equal to the circulation rate divided by the feed rate or discharge rate. For example, as illustrated in FIG. 4A, if the feed rate and the discharge rate equal about 50 ml/min and the circulation rate equals about 100 ml/min, the dialysate can circulate about two times into, through and out of the patient's peritoneum prior to discharge. It should be appreciated that the dialysate can be made to pass along the fluid loop any suitable multiple number of times that approximately equals the circulation rate divided by the feed rate or discharge rate.

Figure 4B:
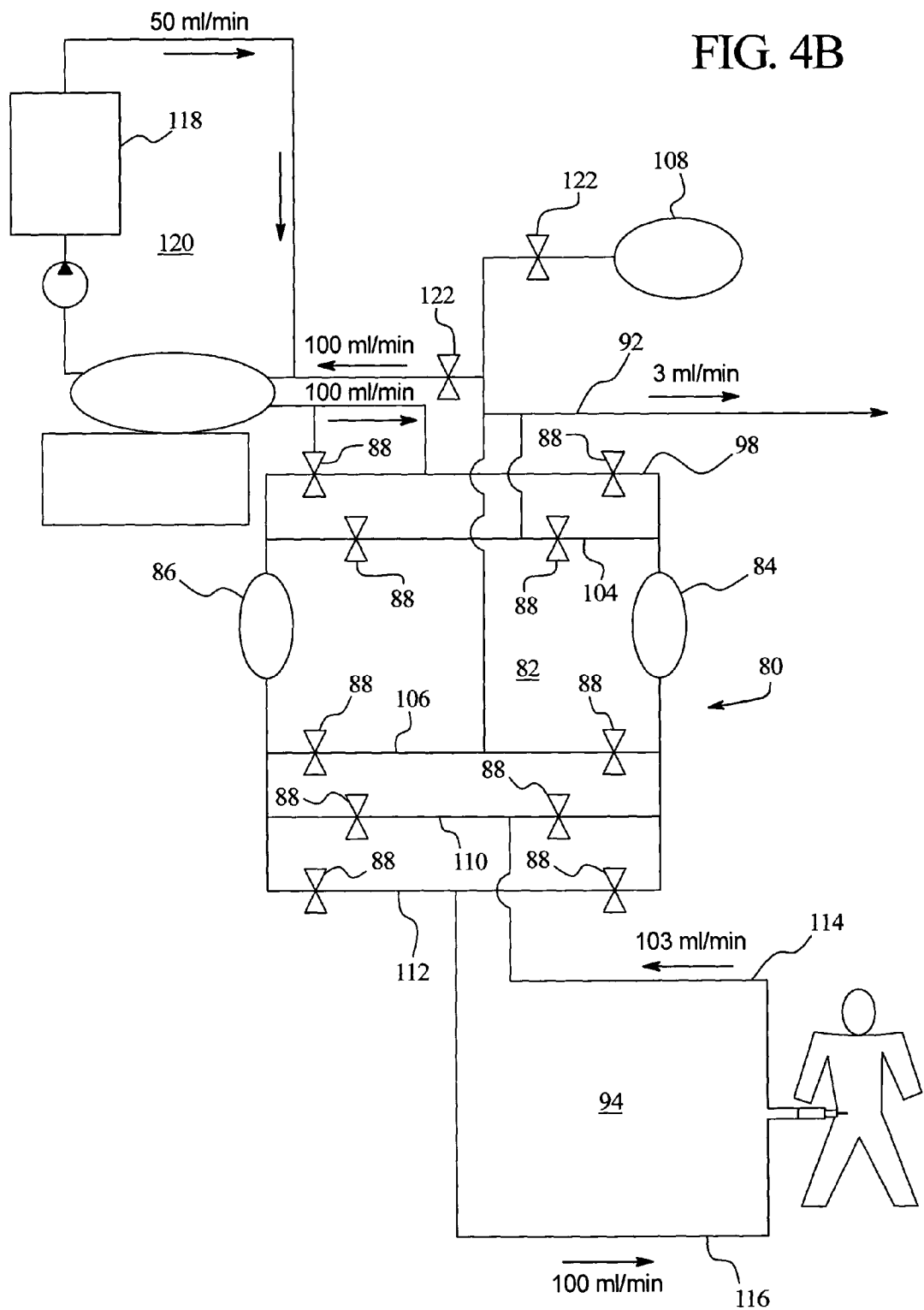
FIG. 4B schematically illustrates an embodiment of the present invention relating to a continuous flow system that utilizes a cycler adapted for automation with a cleaning loop.

As illustrated in FIG. 4B, a cleaning device 118 is coupled to a cleaning fluid loop 120 or path that is coupled to the circulation fluid loop 94 via the cycler 80. In an embodiment, the third fluid line 106 of the cycler as shown in FIG. 4A is modified to accommodate, at separate times during therapy, dialysate that flows into the cleaning fluid loop 120 and a fresh source of dialysate that flows from the last bag 108 into the fluid loop 94 once the continuous flow therapy is complete. This is carried out with the use of two valves 122 or the like, such as clamps, one of which is open at a time.

The remaining components of the fluid circuit as shown in FIG. 4B are essentially the same as the components and fluid circuit of FIG. 4B. Again, the primary difference is that FIG. 4B provides a cleaning fluid loop 120. In such a system, the dialysate flow rate is controlled by the feed rate of fresh dialysate or fresh dialysate mixed with cleaned dialysate from the cleaning loop, the flow rate of the dialysate through the cleaning loop, the discharge rate of dialysate from the circulation fluid loop and the circulation rate of dialysate along the circulation fluid loop. In general, the cleaning loop flow rate is maintained at a lower rate than the circulation rate. For example, the dialysate can pass about two times along the circulation loop prior to discharge if the cleaning rate is about 50 ml/min, the feed rate is about 100 ml/min, the flow rate from the patient loop into the cleaning loop is about 100 ml/min, the in-flow rate of dialysate into the peritoneum along the fluid loop is about 100 ml/min, the out flow rate of dialysate out of the peritoneum along the fluid loop is about 103 ml/min and the discharge rate of dialysate is about 3 ml/min as illustrated in FIG. 4B. It should be appreciated that the dialysate flow rate can be controlled and maintained at any suitable rates such that the dialysate can pass a multiple number of times into and out of the patient's peritoneum prior to discharge.

As previously discussed, the systems and methods of the present invention can accommodate a variable change in therapy fluid volume during treatment. For example, an increase in volume may be due to the removal of ultrafiltrate from the patient, the addition of an osmotic agent solution and/or the like as discussed above. The systems of the present invention can be adapted in any number of suitable ways to accommodate the increase in therapy fluid such that it can be utilized during treatment.

Figure 5A:
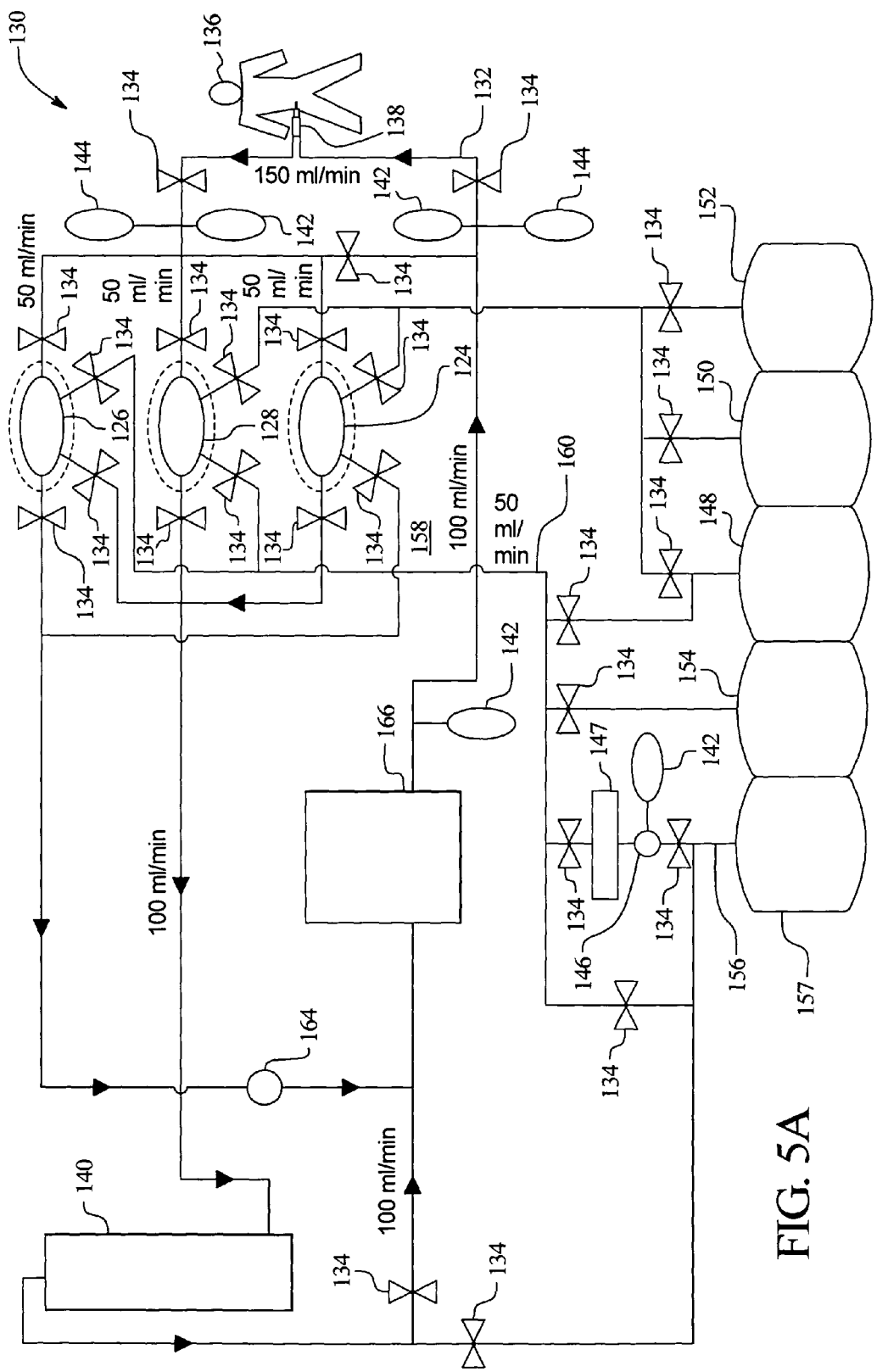
FIG. 5A schematically illustrates a continuous flow peritoneal dialysis system that employs an accumulator bag showing flow out of the fluid loop and into the accumulator bag according to an embodiment of the present invention.
Figure 5B:
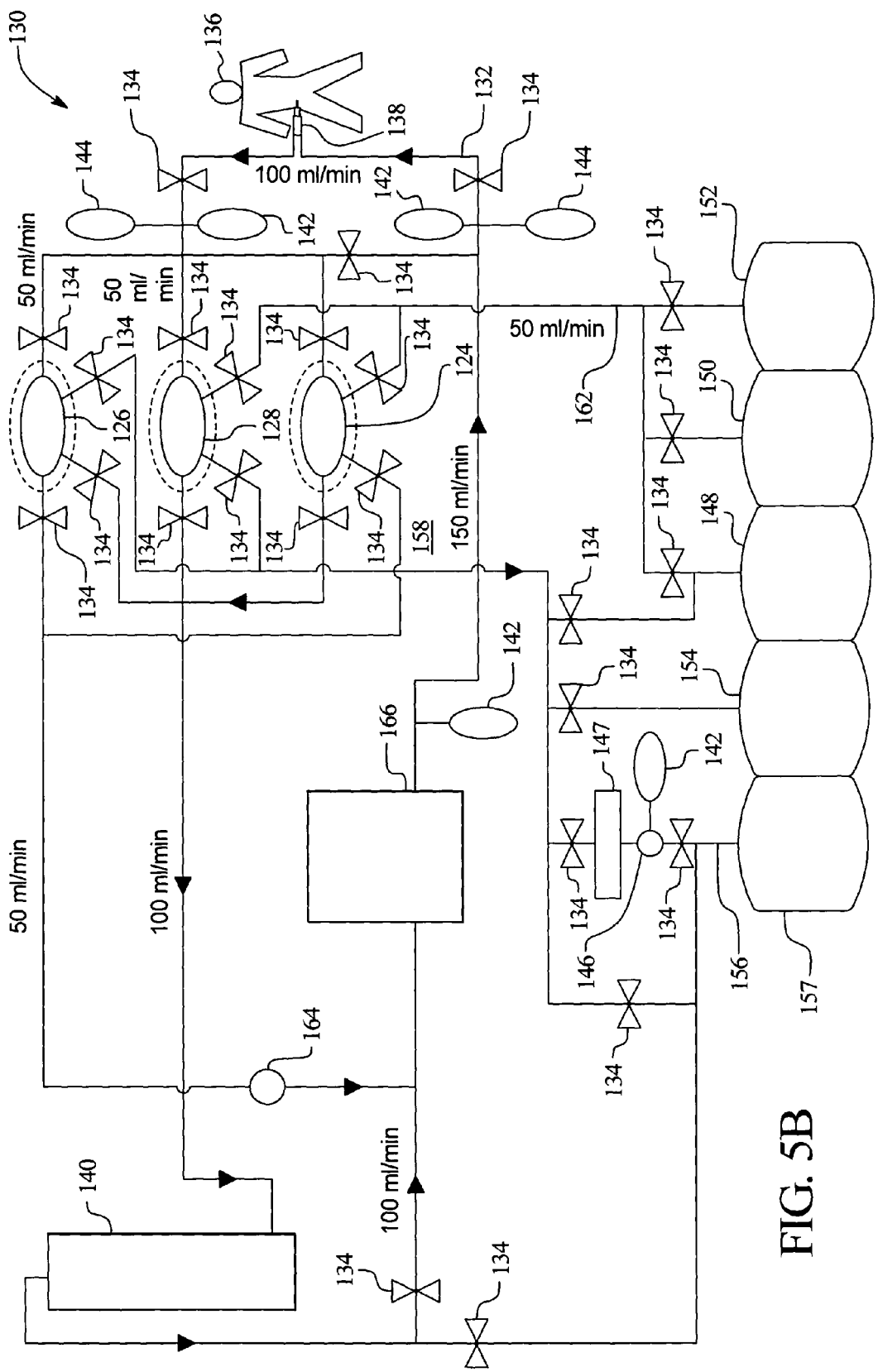
FIG. 5B schematically illustrates a continuous flow peritoneal dialysis system that employs an accumulator bag to move fluid into and out of the fluid loop showing flow into the fluid loop from the accumulator bag according to an embodiment of the present invention.

In an embodiment, the system can include three pumps, such as a third pump 124 in addition to the first pump 126 and second pump 128 of the cycler as shown in FIGS. 5A and 5B. The pumps are connected to the fluid circuit 130 via a number of corresponding fluid lines 132. A number of valves 134 are also coupled to the fluid circuit 130 to control and regulate the flow of therapy fluid during treatment. The fluid circuit 130 is coupled to the patient 136 via a catheter 138 inserted within the patient 136. A cleaning cartridge 140 can also be coupled to the fluid circuit 130 to clean the therapy fluid for reuse as previously discussed. Any suitable number and type of additional other components can be coupled to the fluid circuit 130. For example, temperature sensor(s) 142 and pressure sensor(s) 144 can be coupled to the fluid circuit 130 at any desired location. Further, the fluid circuit 130 can include a chemical sensor, such as a sensor 146 for detecting creatinine levels or the like. A converter 147 can be coupled to the fluid circuit in proximity to the sensor 146.

The dialysate is pumped into the fluid circuit 130 via a supply source 148. The supply source 148 can include any suitable container that can be coupled to the fluid circuit 130 and that can store the dialysate prior to use. In an embodiment, the dialysate includes about 6 liters or less in any suitable amount of an osmotic agent. The dialysate can include any suitable number, type and amount of other components, such as electrolytes including, for example, potassium, calcium, sodium, the like and/or combinations thereof. A concentrate source 150 can also be coupled to the fluid circuit 130. The concentrate source 150 includes any suitable container that can store a concentrate, such as an osmotic agent solution, preferably having a concentration of an osmotic agent greater than the dialysate source. In an embodiment, the concentrate includes about 4.25% or more by weight of an osmotic agent, such as dextrose. The concentrate can also include any suitable amount, type and number of other components, such as electrolytes. In an embodiment, the concentrate volume is about three liters or less.

A last bag 152 of therapy fluid can also be coupled to the fluid circuit. The therapy fluid of the last bag includes any suitable amount and type of a fresh source of dialysate. The last bag volume of dialysate is pumped into the peritoneal cavity of the patient at the end of multipass treatment where it can dwell for a desired period of time and then be drained from the peritoneal cavity along with any metabolic waste and ultrafiltrate that may have been removed from the patient. The treatment cycle that includes multipass treatment followed by a last bag fill, dwell and drain cycle can then be repeated.

A collection chamber 154 can also be coupled to the fluid circuit. This chamber can be utilized to collect a sample(s) of the therapy fluid at a desired time period. Preferably, the therapy fluid is collected every 24 hours. The sample can be analyzed to evaluate treatment performance, such as to determine dialysis clearance levels. The fluid circuit also includes a drain pathway 156 through which the fluid circuit coupled to the patient can be drained of therapy fluid. In an embodiment, the fluid can be drained into a bag 157.

At the beginning of multipass treatment, the initial source of dialysate 148 is pumped into the fluid circuit 130. This can be done in a continuous manner, intermittently, non-continuous, batch or the like depending on the application. The dialysate then circulates along the fluid loop 158 defined by the fluid circuit 130 coupled to the patient 136 such that the dialysate can pass into, through and out of the peritoneal cavity of the patient to remove metabolic waste and ultrafiltrate. The dialysate can be circulated at any suitable flow rate, an example of which is illustrated in FIGS. 5A and 5B.

As the dialysate removes metabolic waste and ultrafiltrate from the patient 136, the therapy fluid can increase in volume. Further, the concentrate 150 can be pumped into the fluid circuit 130 at any suitable time during treatment to facilitate the removal of metabolic waste and ultrafiltrate from the patient as previously discussed. The addition of concentrate can also increase the volume of therapy fluid.

As the therapy fluid volume increases, the dialysate source container 148 can be utilized to accommodate for this increase in therapy fluid. In this regard, a portion of the therapy fluid can be pumped into the dialysate source container 148 along the fluid line 160 and via the second pump 128 as indicated in FIG. 5A. The portion of the therapy fluid can remain in the dialysate source container 148 for any suitable time period after which this portion can be pumped back into the fluid circuit 130 along the fluid line 162 via the third pump 124 as illustrated in FIG. 5B. The pumping of the portion of the therapy fluid into or out of the dialysate source container 148 can occur while the remaining portion of therapy fluid continues to circulate along the fluid circuit 130. That is, the dialysate source container can be filled or drained with a portion of the therapy fluid in parallel to the circulation of the remaining portion of the therapy fluid along the fluid circuit.

It should be appreciated that the system can utilize any suitable type of pumping mechanism in any suitable way to provide circulation of the therapy fluid along the fluid circuit in parallel to flow into and/or out of the dialysate source container. Hereinafter, this type of flow is referred to as tidal CFPD flow. In this regard, FIGS. 5A and 5B convey an illustrative example of tidal flow performed in a system according to an embodiment of the present invention. The system of the present invention can be configured and operated in any suitable number of ways to achieve the desired tidal flow characteristics allowing the system to accommodate a variable increase in therapy fluid volume. For example, the system can include an additional pump, that is, a total of four pumps, to increase the pumping efficiency of the system.

The system can include any suitable number and type of additional other components. For example, the system can include a back flow regulator 164 as shown in FIGS. 5A and 5B. The system can also include a heating mechanism to regulate the temperature of the therapy fluid. For example, the system can include an in-line heater 166 as shown in FIGS. 5A and 5B. The heater 166 can also include a filter or other suitable components, such as an air sensor (not shown). It should be appreciated that any suitable type and/or number of filters can be coupled to the fluid circuit in any suitable manner and at any suitable position(s). For example, the filter (not shown) can be integral to the cleaning cartridge 140 so that it continuously filters the recirculating fluid. In an embodiment, the filter (not shown) can be located in supply line 162 so that it filters fluid from sources 148, 150 and 152 as it is drawn into the system 130.

The filter can be made of any suitable material and include any suitable filter size. In an embodiment, the filter is about 0.3 microns in size, preferably about 0.22 microns. This means that the filter can remove solutes in solutions that are about 0.3 microns in size or larger with a filter size of about 0.3 microns or about 0.22 microns in size or larger for a filter size of about 0.22 microns. The filter can act in a variety of different ways to enhance the performance of the dialysis system of the present invention.

For example, the filter can be used in place of typical UV decontamination techniques or the like to disinfect the therapy fluid prior to passing into, through and out of the patient. This can effectively eliminate, or at least greatly reduce, infection in the patient as a result of the treatment, such as peritonitis which can be contracted through touch contamination during therapy.

It should be appreciated that the filter(s) can be coupled to the fluid circuit at any suitable position. On the patient in flow side, the filter can act to disinfect the dialysate prior to passing into the patient as previously discussed. The filter(s) can also be coupled to the discharge pathway. In this location, the filter can be used to remove nutrients from the therapy fluid prior to discharge. The filter can then be cleaned by, for example, back flushing with a suitable solution, to remove the filtered nutrients for reuse and reintroduction into the patient. The filter can be constructed in any suitable way to enhance its filtering efficiency.

It should be appreciated that the fluid path, fluid circuit and/or fluid loop of the present invention can be made of one or more fluid lines interconnected in any suitable manner. The fluid lines can include any suitable material including a flexible, sterile and inert plastic, such as polyethylene, polystyrene, polypropylene, polyvinyl chloride and/or combinations thereof. In general, the fluid lines are transparent such that the fluid flow through the lines can be visually observed.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. A system for providing peritoneal dialysis to a patient, the system comprising:
a catheter having an inflow lumen and an outflow lumen in communication with the patient's peritoneal cavity; and
a fluid circuit in fluid communication with the catheter, the fluid circuit comprising:
a fluid loop, the fluid loop configured to circulate dialysate into, through and out of a peritoneal cavity of the patient at an outflow rate from the peritoneal cavity greater than an inflow rate to the peritoneal cavity,
a supply of a dialysate coupled to the fluid circuit, and
at least one of a (i) a chamber coupled to the fluid loop through which the dialysate can be fed at a feed rate into the fluid loop, and (ii) a cleaning device coupled to the fluid loop via a cleaning fluid path wherein the dialysate can be fed into the cleaning fluid path and cleaned at a cleaning rate prior to reintroduction into the fluid loop;
a discharge fluid path coupled to the fluid loop; and
a cycler that pumps the dialysate into the fluid circuit at a feed rate and circulates the dialysate at a circulation rate along the fluid loop to remove a therapeutic effective amount of solutes and excess water from the patient, the cycler further configured to drain the dialysate from the fluid circuit at a discharge rate that is less than the circulation rate and at least substantially equal to a difference between the outflow rate and the inflow rate, allowing the dialysate to be circulated a plurality of times along the fluid loop prior to discharge.

2. The system of claim 1 further comprising at least one pressure sensor coupled to the fluid circuit for sensing a pressure.

3. The system of claim 2 wherein the feed rate and the discharge rate are maintained at an approximately equal rate that is about one half of the circulation rate allowing the dialysate to circulate about two times along the fluid loop.

4. The system of claim 1 wherein the feed rate and the discharge rate are maintained at an approximately equal rate that is about one third of the circulation rate such that the dialysate is capable of circulating about three times along the fluid loop.

5. The system of claim 1 wherein the cycler comprises two pumps.

6. The system of claim 1 wherein the cleaning device contains sorbents for adsorbing at least one of urea, phosphate and creatinine.

7. The system of claim 1 wherein the cleaning device contains an ion exchange resin.

8. The system of claim 1 wherein the cleaning device contains at least one electrolyte for addition to the dialysate.

9. The system of claim 1, wherein the cleaning device contains at least three layers.

10. The system of claim 1, the chamber allowing the fluid loop to accommodate a variable increase in the dialysate during treatment.

11. The system of claim 10 wherein the variable increase in dialysate is due to an addition of ultrafiltrate to the fluid loop as the dialysate dialyzes the patient.

12. The system of claim 1 further comprising at least one valve connecting the catheter to the fluid circuit.

13. A system for providing peritoneal dialysis to a patient, the system comprising:
    a catheter having an inflow lumen and outflow lumen in communication with the patient's peritoneal cavity; and
    a fluid circuit in fluid communication with the catheter thereby defining only a single fluid loop capable of circulating dialysate into, through and out of the peritoneal cavity at an outflow rate from the peritoneal cavity greater than an inflow rate to the peritoneal cavity, the fluid circuit comprising:
        a supply of a dialysate coupled to the fluid loop,
        a cleaning device coupled to the fluid loop via a cleaning fluid path wherein the dialysate can be fed into the cleaning fluid path and cleaned at a cleaning rate prior to reintroduction into the fluid loop, and
        a discharge fluid path coupled to the fluid loop; and
    a cycler that pumps the dialysate into the fluid loop at a feed rate and circulates the dialysate along the fluid loop at a circulation rate to remove a therapeutic effective amount of solutes and excess water from the patient, the cycler further configured to drain dialysate at a discharge rate approximately equal to a difference between the outflow rate and the inflow rate, the discharge rate effective to circulate the dialysate a plurality of times along the fluid loop prior to discharge.

14. The system of claim 13 wherein the fluid loop is coupled to the supply of dialysate, the cleaning fluid path and the discharge fluid path via a cycler.

15. The system of claim 14 wherein the cycler includes a fluid circuit coupled to a pumping mechanism and a plurality of valves such that the cycler is capable of automatically controlling the flow of dialysate into and out of the fluid loop during treatment.

16. The system of claim 13 wherein the cleaning device contains a sorbent material capable of non-selective removal of solutes from the dialysate prior to reuse.

17. The system of claim 16 wherein the sorbent material is selected from the group consisting of carbon, activated charcoal and combinations thereof.

18. The system of claim 13 wherein the cleaning device contains an ion exchange resin.

19. The system of claim 13 wherein the cleaning device contains a sorbent material capable of selective removal of solutes from the dialysate.

* * * * *